(12) United States Patent
Erwin

(10) Patent No.: US 8,003,094 B2
(45) Date of Patent: Aug. 23, 2011

(54) CHEMICAL COMBINATION AND METHOD FOR INCREASING DELIVERY OF COENZYME Q10

(76) Inventor: Charles Erwin, Whittier, CA (US)

(*) Notice: Subject to any disclaimer, the term of this patent is extended or adjusted under 35 U.S.C. 154(b) by 0 days.

(21) Appl. No.: 10/876,752

(22) Filed: Jun. 25, 2004

(65) Prior Publication Data

US 2005/0025756 A1 Feb. 3, 2005

Related U.S. Application Data

(60) Provisional application No. 60/482,781, filed on Jun. 25, 2003.

(51) Int. Cl.
*A61K 38/43* (2006.01)
*A61K 31/122* (2006.01)
*A61K 31/355* (2006.01)
*C07C 50/54* (2006.01)
*C07C 51/09* (2006.01)

(52) U.S. Cl. ....... 424/94.1; 514/678; 514/690; 514/458; 554/174

(58) Field of Classification Search .......... 424/94.1; 514/678, 690, 458; 554/174
See application file for complete search history.

(56) References Cited

U.S. PATENT DOCUMENTS

| | | | | |
|---|---|---|---|---|
| 4,882,336 A * | 11/1989 | Tigyi et al. | | 514/283 |
| 5,378,461 A * | 1/1995 | Neigut | | 424/94.1 |
| 6,287,553 B1 * | 9/2001 | Alaluf et al. | | 424/78.03 |
| 6,417,227 B1 * | 7/2002 | Lord et al. | | 514/529 |
| 2003/0232095 A1 * | 12/2003 | Garti et al. | | 424/725 |
| 2004/0092482 A1 * | 5/2004 | Gupta | | 514/62 |
| 2004/0228884 A1 * | 11/2004 | Gupta | | 424/401 |

FOREIGN PATENT DOCUMENTS

EP 198172 A1 * 10/1986
WO WO 0209685 A1 * 2/2002

* cited by examiner

*Primary Examiner* — Rosanne Kosson
(74) *Attorney, Agent, or Firm* — Brooks Kushman PC

(57) ABSTRACT

The present invention relates to a chemical combination and method for increasing delivery of Coenzyme Q10. The chemical combination comprises Coenzyme Q10 mixed with at least one chemical. The at least one chemical includes cyclic monoterpene containing essential oil(s) that permit unprecedented levels of Coenzyme Q10 to be made available for delivery and absorption, increasing bioavailability, as well as overcoming the previous limits.

12 Claims, No Drawings

CHEMICAL COMBINATION AND METHOD FOR INCREASING DELIVERY OF COENZYME Q10

PRIORITY CLAIM

This application is a non-provisional application, claiming the benefit of priority to provisional application No. 60/482,781, filed in the United States on Jun. 25, 2003, entitled, "Increasing Absorption, Rate of Absorption and efficacy and overcoming Coenzyme Q10 solubility and crystallization problems in oral and new delivery systems."

FIELD OF INVENTION

The present invention relates to a chemical combination, and more particularly, to a chemical combination that when combined with Coenzyme Q10, increases stable solubility, absorption, and efficacy of the Coenzyme Q10, and Coenzyme Q10 in its reduced state by a user.

BACKGROUND OF INVENTION

Reactions in the body produce chemicals called oxidants (free radicals). The oxidants damage cells and are generally thought to shorten one's life. As a way to protect the body from this damage, the body produces anti-oxidants such as Coenzyme Q10. Anti-oxidant nutrients terminate free radicals by donating electrons to the free radicals. The anti-oxidants become oxidized as part of the oxidation reduction reaction, however, the oxidized anti-oxidants do not contribute to the highest energy chain reactions as the free radicals do, which cause in excess of 80 diseases.

Found in a cell's mitochondria, Coenzyme Q10 is thought to be the primary limiting factor in the production of energy within each cell that the body uses to improve health. With this knowledge, researchers have attempted to incorporate Coenzyme Q10 into products with hopes of improving an individual's health through the production of more energy. However, studies have shown that while a small portion of Coenzyme Q10 pills get into the blood stream, even less Coenzyme Q10 is absorbed into the cell's mitochondria. Without being sufficiently recovered by the cell's mitochondria, Coenzyme Q10 products are much less effective than they would otherwise be. Thus, a need exists for a chemical combination that when combined with Coenzyme Q10, increases stable solubility, absorption efficacy, and the uptake of Coenzyme Q10, and Coenzyme Q10 in its reduced state by the cell's mitochondria.

SUMMARY OF INVENTION

The present invention relates to a chemical combination for increasing delivery of Coenzyme Q10 to a cell. The chemical combination comprises Coenzyme Q10 mixed with at least one chemical. Through addition of the at least one chemical, the Coenzyme Q10 is able to be overcome solubility problems and be absorbed more readily by a cell and a cell's mitochondria.

The at least one chemical comprises a solvent that functions as a carrier for the Coenzyme Q10 the solvent is selected from a group consisting of cetyl meristoleate, dl-alpha Tocopheryol acetate, dimethyl sulfoxide, and d-limonene.

In another aspect, the at least one chemical further comprises at least one skin buffer for replacing oils stripped from a user's skin as a solvent passes through the user's skin. The at least one skin buffer is selected from a group consisting of dl-alpha Tocopheryol acetate, cetyl myristoleate, gamma linolenic acid, and conjugated linolenic acid.

In yet another aspect, the at least one chemical further comprises at least one anti-oxidant. The at least one anti-oxidant is selected from a group consisting of alpha lipoic acid, d-alpha Tocopheryol Succinate, Vinpocetin, Ergoloid mesylates, and Vitamin(s) A(s), B(s), C(s), D(s), E(s), F(s) and K(s).

Furthermore, the chemical combination is formed in a form suitable for a delivery method selected from a group consisting of inhalation, oral, intramuscular injection, intravenous (IV)-drip, lingual, gum, sub-lingual, nasal, anal, percutaneous transdermal absorption, and transdermal patch.

In another aspect, chemical combination comprises:
the Coenzyme Q10 being approximately 1 to 85 percent by weight of the combination;
the solvent being approximately 10 to 90 percent by weight of the combination;
a first skin buffer being approximately 0 to 30 percent by weight of the combination;
a first anti-oxidant being approximately 0 to 20 percent by weight of the combination; and
a second skin buffer being approximately 0 to 30 percent by weight of the combination; and
a second anti-oxidant being approximately 0 to 20 percent by weight of the combination.

In a further aspect, the chemical combination comprises:
the Coenzyme Q10 being approximately 5 to 30 percent by weight of the combination;
the solvent being approximately 30 to 85 percent by weight of the combination;
a first skin buffer being approximately 1 to 25 percent by weight of the combination;
a first anti-oxidant being approximately 1 to 10 percent by weight of the combination; and
a second skin buffer being approximately 1 to 20 percent by weight of the combination; and
a second anti-oxidant being approximately 1 to 5 percent by weight of the combination.

In yet another aspect, the chemical combination comprises:
the Coenzyme Q10 being approximately 12 to 18 percent by weight of the combination;
the solvent being approximately 65 to 73 percent by weight of the combination;
a first skin buffer being approximately 1 to 20 percent by weight of the combination;
a first anti-oxidant being approximately 1 to 4 percent by weight of the combination; and
a second skin buffer being approximately 6 to 10 percent by weight of the combination; and
a second anti-oxidant being approximately 1 to 3 percent by weight of the combination.

In another aspect, the present invention is a method for applying a chemical combination. The method comprises acts of obtaining the chemical combination and administering the chemical combination to a user.

As can be appreciated by one in the art, the present invention is not limited to the chemical combination itself, but also includes a method for increasing delivery potential of Coenzyme Q10 by forming the chemical combination, and a method for transdermal delivery of Coenzyme Q10 by applying the chemical combination described herein.

DETAILED DESCRIPTION

The present invention relates to a chemical combination, and more particularly, to a chemical combination that when combined with Coenzyme Q10, increases stable solubility, absorption efficacy, and the uptake of Coenzyme Q10, and Coenzyme Q10 in its reduced state by the cell's mitochondria.

The following description, taken in conjunction with the referenced tables, is presented to enable one of ordinary skill in the art to make and use the invention. Various modifications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein. Furthermore, it should be noted that unless explicitly stated otherwise, the numerical values in the tables included herein are illustrated qualitatively and without any specific scale, and are intended to generally present the concept of the present invention.

In order to provide a working frame of reference, first an introduction is provided to provide the reader with a brief understanding of the present invention. Second, a discussion of various aspects of the present invention is provided to give an understanding of the specific details.

(1) Introduction

The present invention comprises a chemical combination for delivering Coenzyme Q10. The chemical combination utilizes a solvent to solve Coenzyme Q10 solubility, crystallization, re-crystallization, shelf life, rate of delivery, percentage delivered, efficacy and re-solublizing below body temperature are problems encountered by nutritional formulators when sufficient Coenzyme Q10 is combined with a carrier(s) for bodily uptake. When applied, the chemical combination of the present invention increases delivery of Coenzyme Q10 to any entity using it, non-limiting examples of which include humans and animals.

The present invention also comprises new methods for delivering the product of the present invention. The delivery methods include inhalation, oral, intramuscular injection, intravenous (IV)-drip, lingual, gum, sub-lingual, nasal, anal and percutaneous transdermal absorption, and transdermal patch.

(2) Discussion

The present invention is a novel and advanced nutritional product that utilizes a solvent to solve Coenzyme Q10 solubility problems with a faster rate of delivery and a higher percentage of the nutritional contents being sufficiently delivered. The solvent is any solvent that functions as a carrier of Coenzyme Q10 or Coenzyme Q10's synergistic compounds, non-limiting examples of which include cetyl meristoleate (CMO), dl-alpha Tocopheryol acetate, dimethyl sulfoxide, and d-limonene singly, and/or with other cyclic monoterpene containing essential oil(s), such as orange oil (which may contain 95% or more d-limonene). Non-limiting examples of d-limonene containing oils include Lavindin, Peppermint, Ginger, Camphor, Geranium, Orange, Lemon, Lavender, Tea Tree, and Rosemary. High dissolution and/or compounding with cyclic monoterpene containing essential oil(s) permits unprecedented levels of Coenzyme Q10 to be made available for delivery and absorption, increasing bioavailability, as well as overcoming the previous limits.

D-limonene combined with Coenzyme Q10 creates a new molecule, which takes in energy when combined with one another. D-limonene may also become a source of energy (fuel) within minutes, enabling the cells (e.g. heart cells) to produce more energy. Additionally, CMO allows d-limonene to be used on the skin, etc.

Bio-availability, taste, fragrance, tissue friendliness and synergistic considerations are addressed further by the addition of buffers and certain anti-oxidants. The term "Buffer" refers to a chemical that is added to a solution with properties sufficient for replacing oils stripped from a user's skin as solvents pass through the user's skin. The buffer may also be both a solvent and/or nutrient, as demonstrated by the present invention. Non-limiting examples of such buffers include dl-alpha Tocopheryol Acetate, lecithin, cetyl myristoleate wax, gamma linolenic acid, and conjugated linolenic acid. The skin buffers also function as anti inflammatory agents and auto-immune inhibitors. Non-limiting examples of such anti-oxidants include alpha lipoic acid, d-alpha Tocopheryol Succinate, Vinpocetin, Ergoloid mesylates, and Vitamins A(s), B(s), C(s), D(s), E(s), F(s) and K(s). The Vitamins would include all forms of each vitamin. For example, non-limiting examples of Vitamin B(s) would include the B3 Vitamins, such as niacinamide, niacin, inositol hexaniacinate, and methyl nicotinate.

The compounds also function as anti-inflammatory agents, anti auto-immune inhibitors, and solvents. Furthermore, anti-oxidants are synergistic with one another, especially vitamin(s) E and C, Coenzyme Q10, and alpha lipoic acid.

The present invention has shown remarkable improvements in cases of late stage congestive heart failure, severe gum disease and tooth abscess, multiple sclerosis, and the immune system functions. It is likely to impact many other diseases, particularly chronic diseases. The present invention also solves other common problems associated with high concentration nutritional products, such as crystallization and re-crystallization, efficacy and resolublizing below body temperature. It is further noted that the present invention may also include formulas designed for other than percutaneous use, which may include high levels of dl-alpha Tocopheryol acetate, and/or lidocaine to buffer tissues and minimize pain associated with the injected material.

It is noted that d-limonene has "generally regarded as safe" (GRAS) status by the Federal Emergency Management Agency (FEMA), located at 500 C Street, SW Washington, D.C. 20472, since 1965 and is approved by the U.S. Food and Drug Administration (FDA), located at 5600 Fishers Lane, Rockville Md. 20857-0001, for food use.

The following example is provided for a further understanding of the invention, however, the invention is not to be construed as limited thereto. It can be appreciated by one in the art that the percentages associated with each ingredient in the chemical combination can be changed and will fluctuate according to the particular application.

EXAMPLE

This example is directed to a specific chemical combination according to the present invention. It is noted that concentrations of at least 1% Coenzyme Q10 and above are also possible. In this example, the 15% concentration is chosen for illustrative purposes only.

The identification and amounts of ingredients are as follows:

| INGREDIENT | APPROXIMATE AMOUNT (% by weight) |
|---|---|
| Coenzyme Q10 | 15 |
| A solvent, such as d-limonene | 70 |
| A first skin buffer, such as cetyl myristoleate | 8 |
| An anti-oxidant, such as alpha lipoic acid powder | 2 |
| A second skin buffer, such as dl-alpha Tocopheryol Acetate | 3 |
| A second anti-oxidant, such as d-alpha Tocopheroyl Succinate | 2 |

The above formulation is prepared by mixing each of the ingredients in a vessel. The size of the vessel depends upon the amount of the solution desired.

In addition, if the solution solidifies, then it may be warmed to any applicable temperature allowing the solution to resolublize, such as to 37 degrees centigrade.

The present invention also comprises a method for increasing delivery of a chemical solution and/or Coenzyme Q10 to a cell and to a cell's mitochondria. The method comprises an act of forming a chemical mixture and/or compound comprised of Coenzyme Q10 and a combination of chemicals.

For further illustration, following is a non-limiting example of a process of creating a chemical combination according to the present invention. In this non-limiting example, one kilogram of a liquid product with a 15% concentration of Coenzyme Q10 is produced, combining the ingredients listed below in the following sequence, amounts and manner:

A. Mixing 150 grams of Coenzyme Q10 powder with 720 grams of d-limonene in a flask;

B. continuously stirring while warming the combination to approximately 37 degrees centigrade;

C. adding 30 liquid grams of dl-alpha Tocopheryol Acetate;

D. adding 10 grams of alpha lipoic acid powder;

E. adding 80 grams of cetyl myristoleate wax;

F. adding 10 grams of d-alpha Tocopheryol Succinate; and

G. sealing the final combination in a flask to minimize loss of volatile components.

It can be appreciated by one in the art that the aforementioned process can be altered and manipulated to achieve any desirable result. For example, should one desire a different concentration of Coenzyme Q10, the amounts included in the combination would be changed. Additionally, the steps by which the chemicals are added can also be altered to achieve the desired result. Furthermore, certain buffers, anti-oxidants, and solvents can be omitted or changed in various combinations thereto.

In another aspect, the chemical mixture of the present invention is formed in such a way that it allows for effective delivery, non-limiting examples of such delivery methods include inhalation, oral, intramuscular injection, IV-drip, lingual, gum, sub-lingual, nasal, anal, percutaneous transdermal absorption, and transdermal patch.

What is claimed is:

1. A composition consisting of:
(a) coenzyme Q10 in an amount from 5 to 30 percent by weight of the total weight of the composition;
(b) a solvent in an amount from 30 to 85 percent by weight of the total weight of the composition, wherein the amount of the solvent is sufficient to dissolve the coenzyme Q10, and wherein the solvent is selected from the group consisting of cetyl myristoleate, dimethyl sulfoxide, d-limonene, the essential oil of lavindin, the essential oil of peppermint, the essential oil of ginger, the essential oil of camphor, the essential oil of geranium, the essential oil of orange, tea tree oil, the essential oil of lavender, an essential oil comprising a cyclic monoterpene, and mixtures thereof;
(c) a first skin buffer in an amount from 1 to 25 percent by weight of the total weight of the composition wherein the first skin buffer is selected from the group consisting of dl-alpha- tocopheryol acetate, cetyl myristoleate, gamma-linolenic acid, conjugated linolenic acid, d-alpha tocopherol, lecithin, and mixtures thereof;
(d) a first anti-oxidant in an amount from 1 to 10 percent by weight of the total weight of the composition;
(e) a second skin buffer in an amount from 1 to 20 percent by weight of the total weight of the composition; and
(f) a second anti-oxidant in an amount of 1 to 5 percent by weight of the total weight of the composition.

2. The composition of claim 1, wherein the second skin buffer is selected from the group consisting of dl-alpha-tocopheryol acetate, cetyl myristoleate, gamma-linolenic acid, conjugated linolenic acid, d-alpha-tocopherol, lecithin, and mixtures thereof.

3. The composition of claim 1, wherein the solvent is d-limonene.

4. The composition of claim 3, wherein the first skin buffer is cetyl myristoleate and the second skin buffer is dl-alpha-tocopheryol acetate.

5. The composition of claim 4, wherein the first anti-oxidant is alpha-lipoic acid and the second anti-oxidant is d-alpha-tocopheryol succinate.

6. The composition of claim 2, wherein the first and second anti-oxidants are independently selected from the group consisting of alpha-lipoic acid, d-alpha-tocopheryol succinate, vinpocetin, an ergoloid mesylate, vitamin A, vitamin C, vitamin D, vitamin E, vitamin K, and mixtures thereof.

7. A composition consisting of:
(a) coenzyme Q10 in an amount from 12 to 18 percent by weight of the total weight of the composition;
(b) a solvent in an amount from 65 to 73 percent by weight of the total weight of the composition, wherein the amount of the solvent is sufficient to dissolve the coenzyme Q10, and wherein the solvent is selected from the group consisting of cetyl myristoleate, dimethyl sulfoxide, d-limonene, the essential oil of lavindin, the essential oil of peppermint, the essential oil of ginger, the essential oil of camphor, the essential oil of geranium, the essential oil of orange, tea tree oil, the essential oil of lavender, an essential oil comprising a cyclic monoterpene, and mixtures thereof;
(c) a first skin buffer in an amount from 1 to 20 percent by weight of the total weight of the composition wherein the first skin buffer is selected from the group consisting of dl-alpha tocopheryol acetate, cetyl myristoleate, gamma-linolenic acid, conjugated linolenic acid, d-alpha-tocopherol, lecithin, and mixtures thereof;
(d) a first anti-oxidant in an amount from 1 to 4 percent by weight of the total weight of the composition;

(e) a second skin buffer in an amount from 6 to 10 percent by weight of the total weight of the composition; and (f) a second anti-oxidant in an amount of 1 to 3 percent by weight of the total weight of the composition.

8. The composition of claim 7, wherein the second skin buffer is selected from the group consisting of dl-alpha-tocopheryol acetate, cetyl myristoleate, gamma-linolenic acid, conjugated linolenic acid, d-alpha-tocopherol, lecithin, and mixtures thereof.

9. The composition of claim 7, wherein the solvent is d-limonene.

10. The composition of claim 9, wherein the first skin buffer is cetyl myristoleate and the second skin buffer is dl-alpha-tocopheryol acetate.

11. The composition of claim 10, wherein the first anti-oxidant is alph-lipoic acid and the second anti-oxidant is d-alpha-tocopheryol succinate.

12. The composition of claim 7, wherein the first and second anti-oxidants are independently selected from the group consisting of alpha-lipoic acid, d-alpha-tocopheryol succinate, vinpocetin, an ergoloid mesylate, vitamin A, vitamin C, vitamin D, vitamin E, vitamin K, and mixtures thereof.

* * * * *